United States Patent [19]

Kollmeyer

[11] 4,225,499
[45] Sep. 30, 1980

[54] PROCESS FOR PREPARING 3-AZABICYCLO(3.1.0)HEXANE-2-CARBONITRILE

[75] Inventor: Willy D. Kollmeyer, Modesto, Calif.

[73] Assignee: Shell Oil Company, Houston, Tex.

[21] Appl. No.: 922,408

[22] Filed: Jul. 6, 1978

[51] Int. Cl.³ ............................................. C07D 209/52
[52] U.S. Cl. ................................................. 260/326.62
[58] Field of Search ............ 260/326.62, 326.2, 326.8; 562/573; 546/215

[56] References Cited

U.S. PATENT DOCUMENTS 2,479,942   8/1949   Lecher et al. ................. 260/465.5 R

OTHER PUBLICATIONS

Poisel et al., Chem. Ber., 108, pp. 2917–2922, (1975).
Schmidt et al., Angew. Chem. Int. Ed., (Engl.), 16, No. 11, pp. 777–778, (1977).
Rappoport, "The Chemistry of the Cyano Group," pp. 84 & 85, Interscience N.Y., 1970.

Primary Examiner—Donald G. Daus
Assistant Examiner—D. B. Springer

[57] ABSTRACT

3-Azabicyclo(3.1.0)hexane-2-carbonitrile, a precursor for preparing 3-azabicyclo(3.1.0)hexane-2-carboxylic acid, a plant male gametocide, is prepared by (a) treating 3-azabicyclo(3.1.0)hexane with a chlorinating agent to form 3-chloro-3-azabicyclo(3.1.0)hexane; (b) treating a solution of that compound with a strong inorganic base and a lower alkanol, to give a solution of the corresponding 3-azabicyclo(3.1.0.)hex-2-ene; (c) treating the solution with an alkali metal bisulfite to form the 2-bisulfite adduct of 3-azabicyclo(3.1.0)hex-2-ene; (d) treating the reaction mixture containing the adduct with an alkali metal cyanide to form 3-azabicyclo(3.1.0)hexane-2-carbonitrile.

3 Claims, No Drawings

PROCESS FOR PREPARING 3-AZABICYCLO(3.1.0)HEXANE-2-CARBONITRILE

BACKGROUND OF THE INVENTION

3-Azabicyclo(3.1.0)hexane-2-carboxylic acid as been found to be an effective plant male gametocide: U.S. Pat. No. 4,047,930 (the compound is designated therein as 2-carboxy-3,4-methanopyrrolidine). The compound exists in the forms of two geometric (i.e., cis, trans) isomers. Each of these isomeric forms exists in the forms of optical isomers. The racemic mixtures of both of the geometric isomer forms are active as plant male gametocides. The naturally occuring L, cis isomer is active as a plant male gametocide; the relative activities of each of the other optical isomer forms have not been determined. The L,cis isomer occurs naturally in the seeds of the American horse chestnut, *Aesculus parviflora*.

3-Azabicyclo(3.1.0)hexane-2-carboxylic acid now can be prepared synthetically by the following route:
(1) 1,2-cyclopropanedicarboxylic acid is treated with benzylamine to form 3-(benzyl)-3-azabicyclo(3.1.0)hexane-2,4-dione (I).
(2) I is selectively reduced to 3-(benzyl)-3-azabicyclo(3.1.0) hexane (II).
(3) II is catalytically hydrogenated to form 3-azabicyclo(3.1.0) hexane (III).
(4) III is chlorinated to give 3-chloro-3-azabicyclo(3.1.0)-hexane (IV).
(5) A solution of IV is treated with a strong inorganic base and a lower alkanol, and solids are removed from the resulting reaction mixture, to give a solution of 3-azabicyclo(3.1.0)hex-2-ene (V).
(6) The solution of V is treated with an alkali metal bisulfite to form the 2-bisulfite adduct (VI) of 3-azabicyclo(3.1.0)hex-2-ene.
(7) The reaction mixture containing VI is treated with an alkali metal cyanide to form 3-azabicyclo(3.1.0)hexane-2-carbonitrile (VII).
(8) VII is treated with barium hydroxide to form the barium salt of 3-azabicyclo(3.1.0)hexane-2-carboxylic acid, which is treated with sulfuric acid to give a mixture of ($\pm$-trans and $\pm$-cis)-3-azabicyclo(3.1.0)hexane-2-carboxylic acid, from which the two racemic mixtures can be isolated, if desired.

DESCRIPTION OF THE INVENTION

This invention is the above-described method for preparing 3-azabicyclo(3.1.0)hexane-2-carbonitrile—i.e., VII, above—from 3-azabicyclo(3.1.0)hexane—i.e., III above—or its hydrochloride salt.

The method for preparing 3-azabicyclo(3.1.0)hexane and its hydrochloride salt described above, is the subject of application Ser. No. 922,407, filed on July 6, 1978 now U.S. Pat. No. 4,183,857, 1/15/79. The disclosures thereof are incorporated herein to describe a method for preparing 3-azabicyclo(3.1.0)hexane, and its hydrochloride salt, the starting materials in the method of this invention.

3-Azabicyclo(3.1.0)hexane-2-carbonitrile also exists as two geometric (cis,trans) isomers, each of which exists in two optically active forms.

According to this invention, 3-azabicyclo(3.1.0)hexane-2-carbonitrile is prepared by the following procedure:

3-Azabicyclo(3.1.0)hexane is chlorinated on the nitrogen atom. If it is in the form of the hydrochloride salt, it may be neutralized by treating the salt with an aqueous solution of an alkali metal hydroxide, separated and chlorinated, or the salt can be chlorinated, directly.

3-Azabicyclo(3.1.0)hexane can be chlorinated by treating it in solution in an inert solvent, such as an ether, with a chlorinating agent containing "active" or "positive" chlorine. These chlorinating agents are compounds in which the chlorine is present, or may be considered to be present, and/or which yield chlorine, in the positive or cationic form—as the chlorinium ion, $Cl^+$. This kind of chlorinating agent is described and exemplified in detail in U.S. Pat. No. 3,449,421. Common specific chlorinating agents of this type are N-chlorosuccinimide, N-chlorourea, and derivatives of hypochlorous acid, such as sodium hypochlorite, calcium hypochlorite, and tertiary-butyl hypochlorite. The chlorination can be conducted in a single solvent, such as an ether, or it may be done in a two (liquid) phase system such as a liquid hydrocarbon/water system. Suitably, the chlorination can be conducted at about, or somewhat below, room temperature. The product can be isolated from the crude reaction mixture by conventional techniques, as illustrated in the example, hereinafter. However, where the treatment is carried out in an ether, the resulting solution of the product can be used in the next step of the process of the invention. It should be noted that the N-chloro intermediate is very unstable, and this fact must be taken into account if one attempts to isolate it by distillation. Note Example 6C.

Alternatively, the hydrochloride salt can be chlorinated directly by treatment with an aqueous solution of an alkali metal hypochlorite, in the presence of sodium bicarbonate. Preferably, the hydrochloride salt is added to a mixture of the solution of the chlorinating agent and the bicarbonate, at a temperature of from about 0° C. to about 15° C. The product can be isolated from the final reaction mixture by extraction with a solvent, such as an ether, the solution being suitable for use in the next step of the process of the invention.

In that next step, the 3-chloro-3-azabicyclo(3.1.0)hexane, in solution in a suitable solvent such as an ether, is treated with an alcoholic—preferably lower alkanolic—solution of a strong inorganic base, such as an alkali metal hydroxide or alkali metal alkoxide, (or, equivalently, an alkali metal in alcohol), to remove hydrogen chloride and to form 3-azabicyclo(3.1.0)hex-2-ene. The treatment is conveniently accomplished by adding the solution of the chloro-amine precursor at a controlled rate to the solution of the base, at a temperature of from about 0° C. to about 20° C. The resulting inorganic salts are removed by filtration or decantation, and the resulting liquid phase, containing 3-azabicyclo(3.1.0)hex-2-ene, is treated with an aqueous solution of sodium bisulfite, to form the 2-bisulfite adduct, at about room temperature. The resulting two-phase mixture is treated with an alkali metal cyanide, at about room temperature, to form a solution of 3-azabicyclo(3.1.0)hexane-2-carbonitrile in the organic phase. The product is isolated by separating the two phases, removing the organic solvent and extracting the residue with a solvent such as an ether, and removing the solvent from the extract.

In these procedures, the reagents, other than the chlorinating agent, are used in essentially equimolar proportions. Preferably, a 50% to 100% excess of the chlorinating agent is used.

The following examples illustrate conduct of the process of the invention in a particular instance. In these examples, the identitites of the starting material, the intermediates and the product all were confirmed by appropriate chemical and spectral analyses.

EXAMPLE 1

(cis,trans)-3-Azabicyclo(3.1.0)hexane-2-carbonitrile (1)

A. A mixture of 11.8 g (0.0855 mol) of N-chlorosuccinimide, 4.16 g (0.05 mol) of 3-azabicyclo(3.1.0)hexane (Ser. No. 922407) and 250 ml ether was stirred at room temperature for 2½ hrs. After filtration, the ethereal solution was washed with water ($2 \times 100$ ml) and brine ($1 \times 50$ ml). The dried ($MgSO_4$) filtrate was carefully concentrated to ca 40 ml total volume (40 cm Vigreux column). The remaining solution, containing 3-chloro-3-azabicyclo(3.1.0)hexane, was added dropwise (30 min) to a cooled (ice-bath) and stirred solution of 3.30 g (0.05 mol) of 85% potassium hydroxide in 25 ml of absolute ethanol. The white suspension was then stoppered and stirred at room temperature overnight (16 hrs). Filtration removed inorganic salts, which were washed with a little ether. The combined filtrate and ether washings, which contained 3-azabicyclo(3.1.0-)hex-2-ene, were treated with 5.20 g (0.05 mol) of sodium bisulfite in 25 ml water. After stirring vigorously for 1 hr at room temperature, the two-phase mixture containing the bisulfite adduct of 3-azabicyclo(3.1.0-)hex-2-ene, was treated with 2.58 (0.05 mol) of 95% sodium cyanide as a solid for 1 hr at room temperature. The upper organic layer was decanted and the aqueous layer was further extracted with ether ($2 \times 100$ ml, decantation). The combined organic layer and ether extracts were concentrated on the rotary evaporator (water aspirator pressure, 70° C.). The oily residue was diluted with 75 ml ether causing a small aqueous phase to separate. The resulting two-phase mixture was dried ($MgSO_4$) and the solvent was evaporated under reduced pressure to give 1, as a light yellow oil. An analytical sample of 1 was a colorless oil, bp: 62° C. (0.005 Torr.).

B. 56.9 g (0.476 mol) of 3-azabicyclo(3.1.0)hexane hydrochloride (Ser. No. 922,407) was added to 150 ml of a saturated solution of potassium hydroxide in water. The separated oil was dissolved in 200 ml of ether, the solution was dried ($MgSO_4$), and 112.5 g (0.842 mole) of N-chlorosuccinimide in 800 ml of ether was added. The mixture was stirred for 3 hrs at room temperature, then filtered, washed with water and sodium chloride solution, dried ($MgSO_4$) and carefully concentrated to about 200 ml volume in a Vigreaux column. The resulting solution was added dropwise over a 30-minute period to a cooled (ice-bath) and stirred solution of 31.4 g (0.476 mol) of 85% potassium hydroxide in 200 ml of absolute ethanol. The resulting suspension was stirred at room temperature overnight, then filtered to remove inorganic salts. The filtrate was treated with 49.5 g (0.476 mol) of sodium bisulfite in 200 ml of water. After stirring for 75 minutes at room temperature, the two-phase mixture was treated with 24.6 g (0.476 mol) of 95% sodium cyanide. The mixture was stirred for 2 hours at room temperature, the organic phase was separated and the aqueous phase was extracted with ether. The combined organic phase and extract was concentrated under reduced pressure. The residue was diluted with 200 ml of ether. A small aqueous phase separated. The two-phase mixture was dried ($MgSO_4$) and stripped of solvent. The residue was distilled to give 1, as a colorless liquid, bp: 58°–61° C. (0.01 Torr.).

C. 12.6 g (0.15 mol) of sodium bicarbonate was added to a cooled (ice-bath) and stirred solution of 5.25% aqueous sodium hypochlorite, 212.7 g (0.15 mol). When most of the bicarbonate had dissolved, 12.0 g (0.10 mol) of 3-azabicyclo(3.1.0)hexane hydrochloride (Ser. No. 922,407) was added. The mixture was stirred (with cooling) for 1 hr, the resulting suspension was extracted with ether. The extract was dried ($MgSO_4$), and divided into two parts. One part was distilled in an attempt to isolate the 3-chloro-3-azabicyclo(3.1.0)hexane. However, the pot residue decomposed suddenly and vigorously when most of the ether had been distilled off, at 36° C. and ambient pressure. The other part of the extract was concentrated to about 25 ml, and was added dropwise to a cooled (ice-bath) and stirred solution of 3.30 (0.05 mol) of 85% potassium hydroxide in absolute ethanol. From this point on, the procedure followed that described in procedure B, above. 1 was obtained as a colorless oil, bp: 52°–54° C. (0.005 Torr.).

EXAMPLE 2

($\pm$-cis)-3-azabicyclo(3.1.0)hexane-2-carboxylic acid, hydrochloride (2) and the ($\pm$-trans)-isomer (3)

A mixture of 34.6 g (0.319 mol) of 1, 102.8 g (0.325 mole) of barium hydroxide octahydrate, and 500 ml of water was refluxed for 7 hrs. The mixture was cooled, and then was carefully neutralized to pH 6 with 33.2 g (0.325 mol) of 96% sulfuric acid in 500 ml of water. Celite was added and the mixture was filtered. The solvent was evaporated and the residue was extracted with hot ethanol. The undissolved solid (2A) was an approximately 2/1 mixture of ($\pm$-trans)- and ($\pm$-cis)-3-azabicyclo(3.1.0)hexane-2-carboxylic acid. The solid obtained from evaporation of the solvent from the extract (7B) was an approximately 2.2/1 mixture of the ($\pm$-cis)- and ($\pm$-trans)-isomers.

2B was subjected to chromatography on a cation exchange resin, using 1.5 N hydrochloric acid as eluent, to give 2, as a solid, mp: 226°–228° C. (with gas evolution), as the more mobile isomer. The less mobile isomer was 3, mp 202°–206° C. (with gas evolution).

I claim:

1. A method for preparing 3-azabicyclo(3.1.0)hexane-2-carbonitrile which consists of the steps:
   (a) treating 3-azabicyclo(3.1.0)hexane with a compound containing active chloride, and forming a solution of 3-chloro-3-azabicyclo(3.1.0)hexane;
   (b) treating said solution with an alcoholic solution of a strong inorganic base and filtering the resulting suspension to give a solution of 3-azabicyclo(3.1.0-)hex-2-ene;
   (c) treating said solution with sodium bisulfite in the presence of water to form the bisulfite adduct,
   (d) treating the resulting mixture with an alkali metal cyanide to form 3-azabicyclo(3.1.0)hexane-2-carbonitrile, and
   (e) isolating said 3-azabicyclo(3.1.0)hexane-2-carbonitrile.

2. A method according to claim 1 in which the 3-azabicyclo(3.1.0)hexane is in solution in an inert solvent when treated by the chlorinating agent.

3. A method according to claim 1 in which the 3-azabicyclo(3.1.0)hexane is in the form of its hydrochloride salt, the chlorinating agent is in water solution, and the resulting reaction mixture is extracted with an inert solvent for 3-chloro-3-azabicyclo(3.1.0)hexane.

* * * * *